US010100082B2

(12) United States Patent
Ghosh et al.

(10) Patent No.: US 10,100,082 B2
(45) Date of Patent: Oct. 16, 2018

(54) HEXAPEPTIDE FOR NEUROPROTECTION AGAINST A β TOXICITY

(71) Applicant: Council of Scientific and Industrial Research, New Delhi (IN)

(72) Inventors: Surajit Ghosh, Kolkata (IN); Atanu Biswas, Kolkata (IN); Batakrishna Jana, Kolkata (IN); Saswat Mohapatra, Kolkata (IN); Subhas Chandra Biswas, Kolkata (IN); Suraiya Saleem, Kolkata (IN); Prasenjit Mondal, Kolkata (IN); Anindyasundar Adak, Kolkata (IN); Subhajit Ghosh, Kolkata (IN); Abhijit Saha, Kolkata (IN); Debmalya Bhunia, Kolkata (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 15/062,773

(22) Filed: Mar. 7, 2016

(65) Prior Publication Data
US 2017/0253631 A1 Sep. 7, 2017

(51) Int. Cl.
| | |
|---|---|
| *A61K 38/00* | (2006.01) |
| *A61P 25/28* | (2006.01) |
| *A61K 9/50* | (2006.01) |
| *A61K 38/04* | (2006.01) |
| *C07K 5/00* | (2006.01) |
| *C07K 7/00* | (2006.01) |
| *C07K 16/00* | (2006.01) |
| *C07K 17/00* | (2006.01) |
| *C07K 7/06* | (2006.01) |
| *A61K 38/08* | (2006.01) |
| *A61K 45/06* | (2006.01) |
| *A61K 9/00* | (2006.01) |

(52) U.S. Cl.
CPC .............. *C07K 7/06* (2013.01); *A61K 9/0019* (2013.01); *A61K 38/08* (2013.01); *A61K 45/06* (2013.01)

(58) Field of Classification Search
CPC .................................. C07K 7/06; A61K 38/08
See application file for complete search history.

(56) References Cited

U.S. PATENT DOCUMENTS 8,324,166 B2 * 12/2012 Gozes .................... A61K 38/08
514/17.7

OTHER PUBLICATIONS

Biswas et al. "Novel Hexapeptide Interacts with Tubulin and Microtubules, Inhibits Abeta Fibrillation, and Shows Significant Neuroprotection" ACS Chemical Neuroscience 6:1309-1316. Published Jul. 6, 2015.*
Feng et al. "Analysis of collinear regions of Oryza AA and CC genomes" J. Genetics and Genomics 36:667-677. Published 2009.*
STN Registry Records containing NAVSIQ. Searched Feb. 6, 2017.*
Barrow, Colin J., et al., "Solution Structures of B Peptide and Its Constituent Fragments: Relation to Amyloid Deposition", *Science*. vol. 253. (1991), 179-182.
Bieler, S., et al., "β-Sheet Breakers for Alzheimer's Disease Therapy", *Current Drug Targets*, 5, (2004), 553-558.
Biswas, Atanu, et al., "An amyloid inhibitor octapeptide forms amyloid type fibrous aggregates and affects microtubule motility", *Chem. Commun.*, 50, (2014), 2604-2607.
Biswas, Atanu, et al., "An amyloid inhibitor octapeptide forms amyloid type fibrous aggregates and affects microtubule motility", Supporting Information, *Chem. Commun.*, 50, (2014), 9 pgs.
Biswas, Subhas C., et al., "Nerve Growth Factor (NGF) Down-regulates the Bcl-2 Homology 3 (BH3) Domain-only Protein Bim and Suppresses Its Proapoptotic Activity by Phosphorylation", *The Journal of Biological Chemistry*, 277(51), (2002), 49511-49516.
Bonne, Dominique, et al., "4',6-Diamidino-2-phenylindole,a Fluorescent Probe for Tubulinan and Microtubules", *The Journal of Biological Chemistry*, 260(5), (1985), 2819-2825.
Cattaneo, Antonino, et al., "Nerve Growth Factor and Alzheimer's Disease: New Facts for an Old Hypothesis", *Mol Neurobiol*, 46, (2012), 588-604.
Chakraborti, Soumyananda, et al., "Curcumin recognizes a unique binding site of tubulin", Supporting Information, *Journal of Medicinal Chemistry*, 54, (2011), 27 pgs.
Chakraborti, Soumyananda, et al., "Curcumin Recognizes a Unique Binding Site of Tubulin", *Journal of Medicinal Chemistry*, 54, (2011), 6183-6196.
Crescenzi, Orlando, et al., "Solution structure of the Alzheimer amyloid β-peptide (1-42) in an apolar microenvironment. Similarity with a virus fusion domain", *Eur. J. Biochem.* 269, (2002), 642-5648.

(Continued)

*Primary Examiner* — Christina Bradley
*Assistant Examiner* — Zachary J Miknis
(74) *Attorney, Agent, or Firm* — Schwegman Lundberg & Woessner, P.A.

(57) ABSTRACT

The present investigation involves designing of a novel hexapeptide, which spontaneously self-assembles to form nanovesicles in physiological conditions. This peptide not only strongly binds with β-tubulin near taxol binding site, but also binds with microtubule lattice in-vitro, as well as intracellular microtubule networks. Interestingly, it inhibits amyloid fibril formation upon co-incubation with Aβ peptide in-vitro and shows excellent neuroprotection against Aβ infected neuronal cell (PC12). Present invention provides a novel approach to produce a peptide-based therapeutics for neurodegenerative disease.

3 Claims, 15 Drawing Sheets
Specification includes a Sequence Listing.

(56) References Cited

OTHER PUBLICATIONS

Gordon, David J., et al., "Inhibition of β-Amyloid(40) Fibrillogenesis and Disassembly of β-Amyloid(40) Fibrils by Short β-Amyloid Congeners Containing N-Methyl Amino Acids at Alternate Residues", *Biochemistry*, 40, (2001), 8237-8245.
Greene, Lloyd A., et al., "Establishment of a noradrenergic clonal line of rat adrenal pheochromocytoma cells which respond to nerve growth factor", *Proc. Natl. Acad. Sci. USA*, 73(7), (Jul. 1976), 2424-2428.
Laferla, Frank M., et al., "Intracellular amyloid-β in Alzheimer's disease", *Nature Reviews Neuroscience*, vol. 8, (Jul. 2007), 499-509.
Luhrs, Thorsten, et al., "3D structure of Alzheimer's amyloid-β(1-42) fibrils", *Proc. Natl. Acad. Sci. USA*, 102(48), (2005), 17342-17347.
Masters, Colin L., et al., "Amyloid plaque core protein in Alzheimer disease and Down syndrome", *Proc. Natl. Acad. Sci. USA*, vol. 82, (Jun. 1985), 4245-4249.
Matrone, Carmela, et al., "Activation of the Amyloidogenic Route by NGF Deprivation Induces Apoptotic Death in PC12 Cells", *Journal of Alzheimer's Disease*, 13(1), (2008), 81-96.
Sanphui, Priyankar, et al., "Efficacy of Cyclin Dependent Kinase 4 Inhibitors as Potent Neuroprotective Agents against Insults Relevant to Alzheimer's Disease", *PLoS ONE*, 8(11):e78842, (Nov. 2013), 1-13.
Xu, Zhiheng, et al., "The MLK Family Mediates c-Jun N-Terminal Kinase Activation in Neuronal Apoptosis", *Molecular and Cellular Biology*, 21(14), (Jul. 2001), 4713-4724.

\* cited by examiner

Figure 1A
Figure 1B
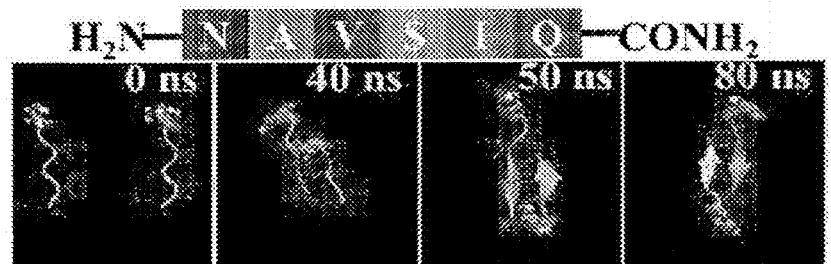
Figure 1C
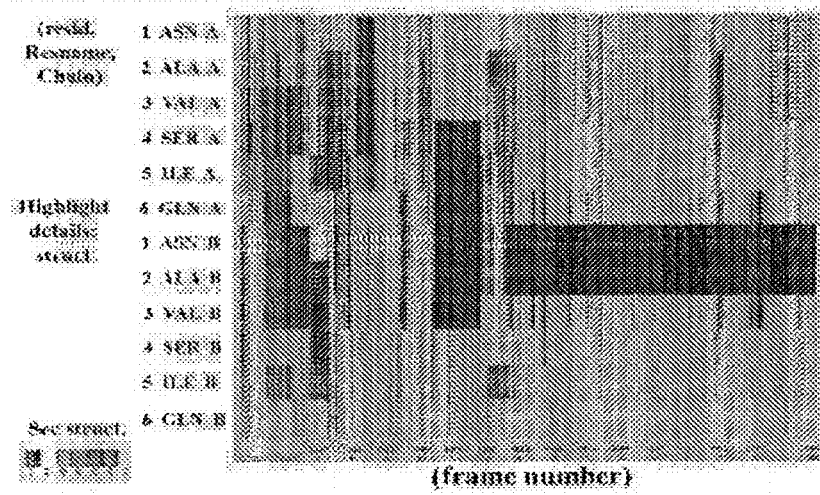
T = Turn, E = β-sheet, B = Isolated bridge, H = Alpha Helix, G = 3₁₀ Helix, I = Pi Helix, C = Random coil
Figure 1D
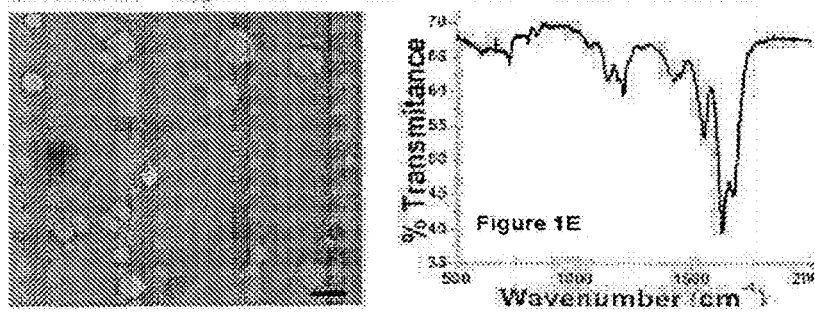
Figure 1E

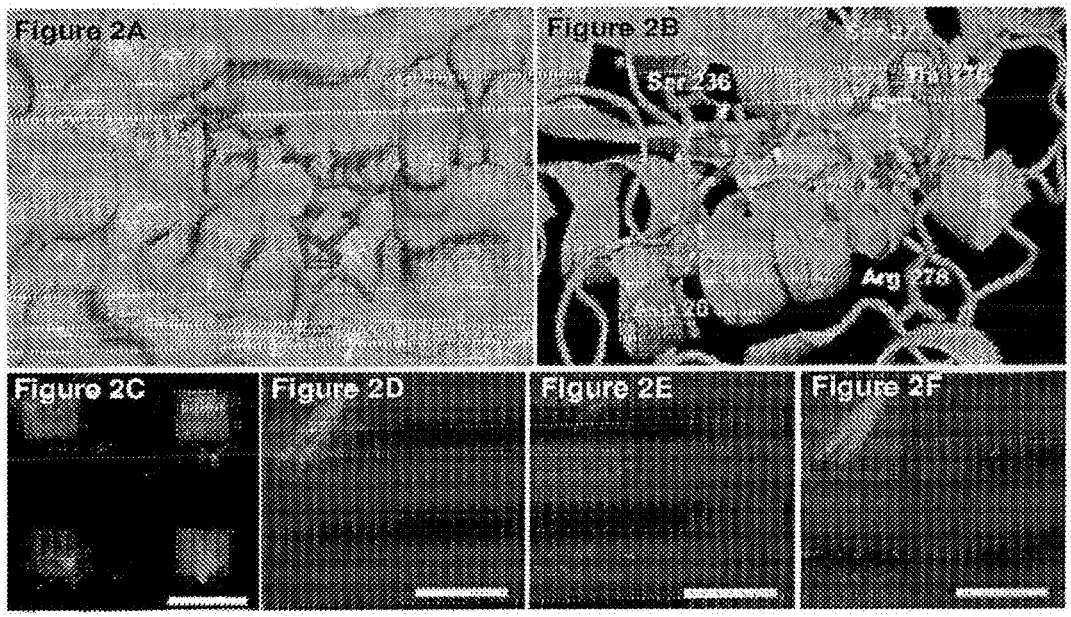

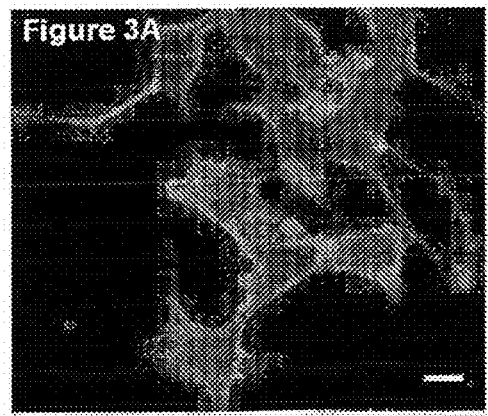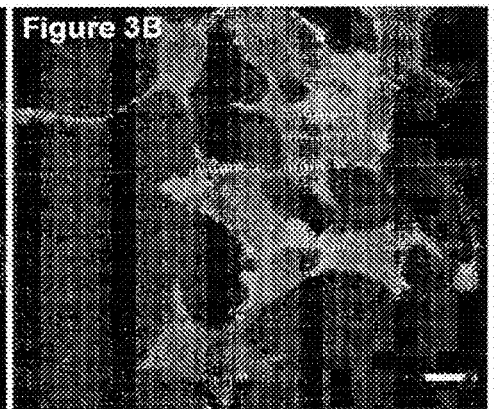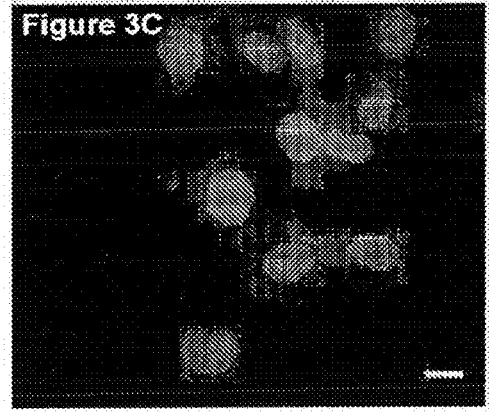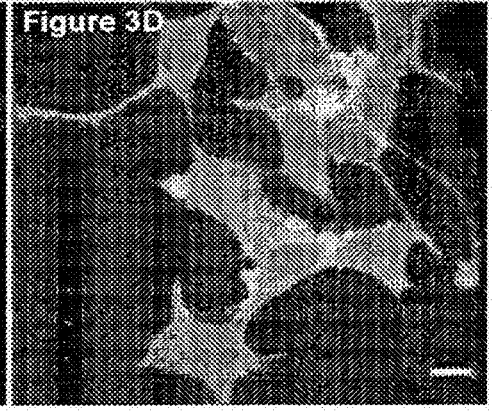

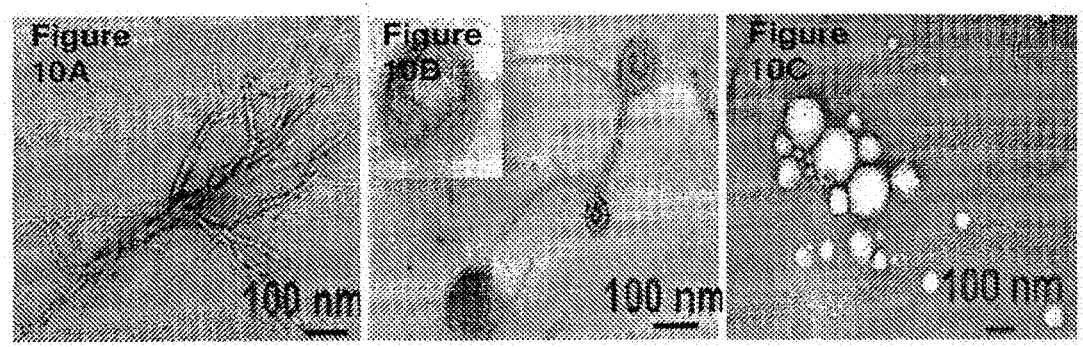

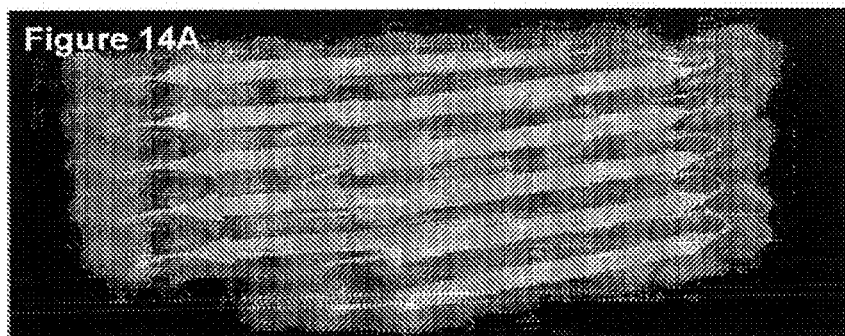
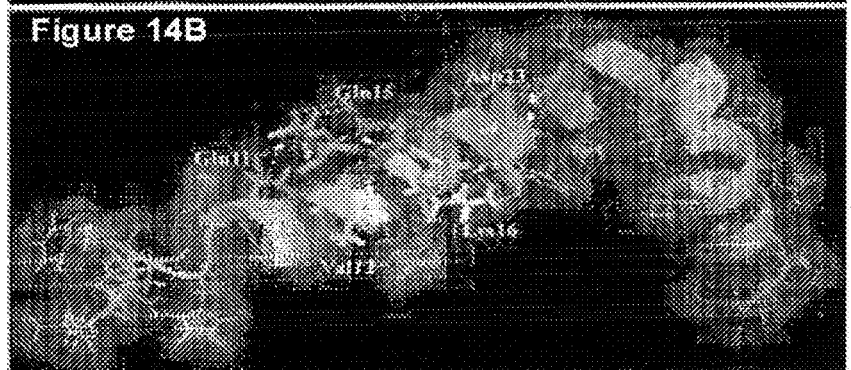
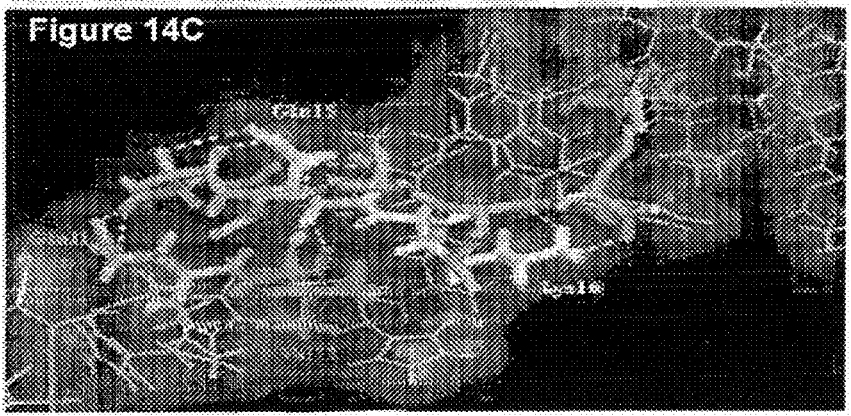

HEXAPEPTIDE FOR NEUROPROTECTION AGAINST A β TOXICITY

SEQUENCE LISTING

This document incorporates by reference herein an electronic sequence listing text file, which is filed in electronic format via EFS-Web. The text file is named "1553710.txt," is 4,096 bytes, and was created on Mar. 7, 2016.

FIELD OF INVENTION

A novel short hexapeptide designed and synthesized for neuroprotection against Aβ toxicity, which shows excellent binding ability to the neurofilament such as microtubules.

BACKGROUND OF THE INVENTION

In our previous study we found that an octapeptide NAPVSIPQ (SEQ ID NO: 2; NQ)[1] inhibits amyloid beta fibrillation in vitro and in vivo tau hyper phosphorylation. Recently, we have also found that NQ, which is known to inhibit tau hyper phosphorylation in vivo, spontaneously forms amyloid like fibrils and inhibits amyloid fibril formation in vitro. Although it shows potential in in vivo studies, but success rate in clinical stage is still poor.

OBJECTIVES OF THE INVENTION

An objective of the present invention is to provide a molecule that can inhibit amyloid beta fibrillation as a neuro-protective therapeutic. Although there are few molecules, like clioquinol which show potential in in-vivo studies, success rate in clinical stage is poor. So, the ultimate goal is to design a novel peptide which can inhibit amyloid beta fibril formation, thus acting as neuro-protective agent.

Another objective of the present invention is to develop a peptide-based drug against Alzheimer's disease which is effective, feasible and less cytotoxic.

SUMMARY OF THE INVENTION

In an aspect of the present disclosure, there is provided a peptide as set forth in SEQ ID NO: 1.

In an aspect of the present disclosure, there is provided a nanovesicle having size in the range of 50-600 nm comprising monomeric units of a peptide as set forth in SEQ ID NO: 1.

In an aspect of the present disclosure, there is provided a method for treatment of Alzheimer's disease in a subject comprising administering a single or multi-dose effective amount of a peptide as set forth in SEQ ID NO: 1; or a nanovesicle having size in the range of 50-600 nm comprising monomeric units of a peptide as set forth in SEQ ID NO: 1.

In an aspect of the present disclosure, there is provided a method for delaying onset of Alzheimer's disease in a subject comprising administering a single or multi-dose effective amount of a peptide as set forth in SEQ ID NO: 1; or a nanovesicle having size in the range of 50-600 nm comprising monomeric units of a peptide as set forth in SEQ ID NO: 1.

In an aspect of the present disclosure, there is provided a peptide as set forth in SEQ ID NO: 1 for prophylactic or curative use in treating Alzheimer's disease.

In an aspect of the present disclosure, there is provided a nanovesicle having size in the range of 50-600 nm comprising monomeric units of a peptide as set forth in SEQ ID NO: 1 for prophylactic or curative use in treating Alzheimer's disease.

In an aspect of the present disclosure, there is provided a peptide as set forth in SEQ ID NO: 1 further modified for enhanced stability and/or imaging.

In an aspect of the present disclosure, there is provided a nanovesicle having size in the range of 50-600 nm comprising monomeric units of a peptide as set forth in SEQ ID NO: 1 further modified for enhanced stability and/or imaging.

In an aspect of the present disclosure, there is provided a method of preparing a nanovesicle having size in the range of 50-600 nm comprising monomeric units of a peptide as set forth in SEQ ID NO: 1.

These and other features, aspects, and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

BRIEF DESCRIPTION OF THE ACCOMPANYING DRAWINGS

The following drawings form part of the present specification and are included to further illustrate aspects of the present disclosure. The disclosure may be better understood by reference to the drawings in combination with the detailed description of the specific embodiments presented herein.

FIG. 1A depicts the amino acid sequence of peptide of SEQ ID NO: 1, in accordance with an embodiment of the present disclosure.

FIG. 1B depicts snapshots of various time-points from MS simulation of peptide of SEQ ID NO: 1 assembly into anti-parallel beta-sheet structures, in accordance with an embodiment of the present disclosure.

FIG. 1C depicts the amino acid residues of peptide of SEQ ID NO: 1 involved in beta-sheet structure formation, in accordance with an embodiment of the present disclosure.

FIG. 1D depicts the self-assembled nanovesicles of peptide of SEQ ID NO: 1, in accordance with an embodiment of the present disclosure.

FIG. 1E depicts the FT-IR spectrum of one hour incubated sample of peptide of SEQ ID NO: 1 forming beta sheet structure, in accordance with an embodiment of the present disclosure.

FIG. 2A depicts the docking image of interaction of peptide of SEQ ID NO: 1 with beta tubulin through hydrophobic interactions, in accordance with an embodiment of the present disclosure.

FIG. 2B depicts the specific amino acid interactions between peptide of SEQ ID NO: 1 and beta tubulin, in accordance with an embodiment of the present disclosure.

FIG. 2C depicts the images of tubulin binding with peptide of SEQ ID NO: 1, immobilized on biotin micro patterned surfaces, in accordance with an embodiment of the present disclosure.

FIG. 2D depicts the Alexa-568 labelled polymerized microtubules, in accordance with an embodiment of the present disclosure.

FIG. 2E depicts the FITC labelled peptide of SEQ ID NO: 1 binding with polymerized microtubules, in accordance with an embodiment of the present disclosure.

FIG. 2F depicts the merged images as depicted in FIG. 2D and FIG. 2E, in accordance with an embodiment of the present disclosure.

FIG. 3A depicts the microtubule network of PC12 cells at 561 nm channel, in accordance with an embodiment of the present disclosure.

FIG. 3B depicts the distribution of nanoparticles comprising peptide of SEQ ID NO: 1 in PC12 cells at 488 nm along microtubule network, in accordance with an embodiment of the present disclosure.

FIG. 3C depicts the nucleus is PC12 cells at 405 nm, in accordance with an embodiment of the present disclosure.

FIG. 3D depicts the merged images of FIGS. 3A-3C, in accordance with an embodiment of the present disclosure.

FIG. 4A depicts the Aβ fibre formation, in accordance with an embodiment of the present disclosure.

FIG. 4B depicts the fibril structures formed upon incubation with Aβ peptide and peptide of SEQ ID NO: 1, in accordance with an embodiment of the present disclosure.

FIG. 4C depicts the interacting partner of Aβ peptide, and peptide of SEQ ID NO: 1, in accordance with an embodiment of the present disclosure.

FIG. 4D depicts the protective effect of peptide of SEQ ID NO: 1 in PC12 cells treated with anti-NGF, in accordance with an embodiment of the present disclosure.

FIG. 4E depicts the graphical representation of percentage of cell survival after anti-NGF treatment in presence of various concentrations of peptide of SEQ ID NO: 1, in accordance with an embodiment of the present disclosure.

FIG. 4F depicts the graphical representation of the protective effect of peptide of SEQ ID NO: 1 compared to octapeptide of SEQ ID NO: 2 in cells treated with anti-NGF, in accordance with an embodiment of the present disclosure.

FIG. 5 depicts the HPLC chromatogram of a peptide of SEQ ID NO: 1 showing purity of >98%, in accordance with an embodiment of the present disclosure.

FIG. 6 depicts the MASS data of a peptide of SEQ ID NO: 1 showing 630 Da, in accordance with an embodiment of the present disclosure.

FIG. 7 depicts the HLPC chromatogram of a biotin labelled peptide of SEQ ID NO: 1 of 878 Da, in accordance with an embodiment of the present disclosure.

FIG. 8 depicts the MASS data of biotin labelled peptide of SEQ ID NO: 1 showing 878 Da, in accordance with an embodiment of the present disclosure.

FIG. 9 depicts the time lapse images of peptide of SEQ ID NO: 1 showing transformation of four peptides to form antiparallel beta sheet structure, in accordance with an embodiment of the present disclosure.

FIG. 10A depicts TEM image of nanovesicular structure of units of peptide of SEQ ID NO: 1 after 1 day, in accordance with an embodiment of the present disclosure.

FIG. 10B depicts the TEM image of nanovesicular structure of units of peptide of SEQ ID NO: 1 after 2 days, in accordance with an embodiment of the present disclosure.

FIG. 10C depicts the TEM image of nanovesicular structure of units of peptide of SEQ ID NO: 1 after 3 days, in accordance with an embodiment of the present disclosure.

FIG. 11A depicts the docking of peptide of SEQ ID NO: 1 with beta tubulin, in accordance with an embodiment of the present disclosure.

FIG. 11B depicts the amino acids of peptide of SEQ ID NO: 1 and beta tubulin involved in H-bonding, in accordance with an embodiment of the present disclosure.

FIG. 12A depicts the 2D view of binding site structure of taxol with tubulin dimer, in accordance with an embodiment of the present disclosure.

FIG. 12B depicts the 2D view of peptide of SEQ ID NO: 1 with tubulin dimer, in accordance with an embodiment of the present disclosure.

FIGS. 13A-13B depict the tubulin turbidity assay in presence of peptide of SEQ ID NO: 1, in accordance with an embodiment of the present disclosure.

FIGS. 14A-14C depict the structure modelling of peptide of SEQ ID NO: 1 with A-beta sheets, in accordance with an embodiment of the present disclosure.

DETAILED DESCRIPTION OF THE INVENTION

Those skilled in the art will be aware that the present disclosure is subject to variations and modifications other than those specifically described. It is to be understood that the present disclosure includes all such variations and modifications. The disclosure also includes all such steps, features, compositions and compounds referred to or indicated in this specification, individually or collectively, and any and all combinations of any or more of such steps or features.

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods, and materials are now described. All publications mentioned herein are incorporated herein by reference.

The present disclosure is not to be limited in scope by the specific embodiments described herein, which are intended for the purposes of exemplification only. Functionally-equivalent products, compositions, and methods are clearly within the scope of the disclosure, as described herein.

Sequences:
SEQ ID NO: 1 NAVSIQ.
SEQ ID NO: 2 NAPVSIPQ.

In an embodiment of the present disclosure, there is provided a peptide as set forth in SEQ ID NO: 1.

In an embodiment of the present disclosure, there is provided a nanovesicle having size in the range of 50-600 nm comprising monomeric units of a peptide as set forth in SEQ ID NO: 1.

In an embodiment of the present disclosure, there is provided a method of treatment of Alzheimer's disease in a subject comprising administering a single or multi-dose effective amount of a peptide as set forth in SEQ ID NO: 1; or a nanovesicle having size in the range of 50-600 nm comprising monomeric units of a peptide as set forth in SEQ ID NO: 1.

In an embodiment of the present disclosure, there is provided a method of treatment of Alzheimer's disease as described herein, said method optionally further comprising concurrent administration of at least one more neuroprotective therapeutic agent to said subject.

In an embodiment of the present disclosure, there is provided a method of treatment of Alzheimer's disease as described herein, said method further comprising concurrent administration of at least one more neuroprotective therapeutic agent to said subject.

In an embodiment of the present disclosure, there is provided a method of treatment of Alzheimer's disease as described herein, wherein administration of said peptide is intravenous.

In an embodiment of the present disclosure, there is provided a method of treatment of Alzheimer's disease as described herein, wherein administration of said nanovesicle is intravenous.

In an embodiment of the present disclosure, there is provided a method of treatment of Alzheimer's disease in a subject comprising administering a single effective amount of a peptide as set forth in SEQ ID NO: 1.

In an embodiment of the present disclosure, there is provided a method of treatment of Alzheimer's disease in a subject comprising administering a single effective amount of a peptide as set forth in SEQ ID NO: 1, and concurrently at least one more neuroprotective agent.

In an embodiment of the present disclosure, there is provided a method of treatment of Alzheimer's disease in a subject comprising intravenous administration a single effective amount of a peptide as set forth in SEQ ID NO: 1.

In an embodiment of the present disclosure, there is provided a method of treatment of Alzheimer's disease in a subject comprising intravenous administration a single effective amount of a peptide as set forth in SEQ ID NO: 1, and concurrently at least one more neuroprotective agent.

In an embodiment of the present disclosure, there is provided a method of treatment of Alzheimer's disease in a subject comprising administering a multi-dose effective amount of a peptide as set forth in SEQ ID NO: 1.

In an embodiment of the present disclosure, there is provided a method of treatment of Alzheimer's disease in a subject comprising administering a multi-dose effective amount of a peptide as set forth in SEQ ID NO: 1, and concurrently at least one more neuroprotective agent.

In an embodiment of the present disclosure, there is provided a method of treatment of Alzheimer's disease in a subject comprising intravenous administration a multi-dose effective amount of a peptide as set forth in SEQ ID NO: 1.

In an embodiment of the present disclosure, there is provided a method of treatment of Alzheimer's disease in a subject comprising intravenous administration of a multi-dose effective amount of a peptide as set forth in SEQ ID NO: 1, and concurrently at least one more neuroprotective agent.

In an embodiment of the present disclosure, there is provided a method of treatment of Alzheimer's disease in a subject comprising administering a single effective amount of a nanovesicle having size in the range of 50-600 nm comprising monomeric units of a peptide as set forth in SEQ ID NO: 1.

In an embodiment of the present disclosure, there is provided a method of treatment of Alzheimer's disease in a subject comprising administering a single effective amount of a nanovesicle having size in the range of 50-600 nm comprising monomeric units of a peptide as set forth in SEQ ID NO: 1, and concurrently at least one more neuroprotective agent.

In an embodiment of the present disclosure, there is provided a method of treatment of Alzheimer's disease in a subject comprising intravenous administration of a single effective amount of a nanovesicle having size in the range of 50-600 nm comprising monomeric units of a peptide as set forth in SEQ ID NO: 1.

In an embodiment of the present disclosure, there is provided a method of treatment of Alzheimer's disease in a subject comprising intravenous administration of a single effective amount of a nanovesicle having size in the range of 50-600 nm comprising monomeric units of a peptide as set forth in SEQ ID NO: 1, and concurrently at least one more neuroprotective agent.

In an embodiment of the present disclosure, there is provided a method of treatment of Alzheimer's disease in a subject comprising administering a multi-dose effective amount of a nanovesicle having size in the range of 50-600 nm comprising monomeric units of a peptide as set forth in SEQ ID NO: 1.

In an embodiment of the present disclosure, there is provided a method of treatment of Alzheimer's disease in a subject comprising administering a multi-dose effective amount of a nanovesicle having size in the range of 50-600 nm comprising monomeric units of a peptide as set forth in SEQ ID NO: 1, and concurrently at least one more neuroprotective agent.

In an embodiment of the present disclosure, there is provided a method of treatment of Alzheimer's disease in a subject comprising intravenous administration of a multi-dose effective amount of a nanovesicle having size in the range of 50-600 nm comprising monomeric units of a peptide as set forth in SEQ ID NO: 1.

In an embodiment of the present disclosure, there is provided a method of treatment of Alzheimer's disease in a subject comprising intravenous administration of a multi-dose effective amount of a nanovesicle having size in the range of 50-600 nm comprising monomeric units of a peptide as set forth in SEQ ID NO: 1, and concurrently at least one more neuroprotective agent.

In an embodiment of the present disclosure, there is provided a method for delaying onset of Alzheimer's disease in a subject comprising administering a single or multi-dose effective amount of a peptide as set forth in SEQ ID NO: 1; or a nanovesicle having size in the range of 50-600 nm comprising monomeric units of a peptide as set forth in SEQ ID NO: 1.

In an embodiment of the present disclosure, there is provided a method for delaying onset of Alzheimer's disease as described herein, said method optionally further comprising concurrent administration of at least one more neuroprotective therapeutic agent to said subject.

In an embodiment of the present disclosure, there is provided a method for delaying onset of Alzheimer's disease as described herein, said method further comprising concurrent administration of at least one more neuroprotective therapeutic agent to said subject.

In an embodiment of the present disclosure, there is provided a method for delaying onset of Alzheimer's disease as described herein, wherein administration of said peptide is intravenous.

In an embodiment of the present disclosure, there is provided a method for delaying onset of Alzheimer's disease as described herein, wherein administration of said nanovesicle is intravenous.

In an embodiment of the present disclosure, there is provided a method for delaying onset of Alzheimer's disease comprising administering a single effective amount of a peptide as set forth in SEQ ID NO: 1.

In an embodiment of the present disclosure, there is provided a method for delaying onset of Alzheimer's disease comprising administering a single effective amount of a peptide as set forth in SEQ ID NO: 1, and concurrently at least one more neuroprotective agent.

In an embodiment of the present disclosure, there is provided a method for delaying onset of Alzheimer's disease comprising intravenous administration a single effective amount of a peptide as set forth in SEQ ID NO: 1.

In an embodiment of the present disclosure, there is provided a method for delaying onset of Alzheimer's disease comprising intravenous administration a single effective amount of a peptide as set forth in SEQ ID NO: 1, and concurrently at least one more neuroprotective agent.

In an embodiment of the present disclosure, there is provided a method for delaying onset of Alzheimer's disease comprising administering a multi-dose effective amount of a peptide as set forth in SEQ ID NO: 1.

In an embodiment of the present disclosure, there is provided a method for delaying onset of Alzheimer's disease comprising administering a multi-dose effective amount of a peptide as set forth in SEQ ID NO: 1, and concurrently at least one more neuroprotective agent.

In an embodiment of the present disclosure, there is provided a method for delaying onset of Alzheimer's disease comprising intravenous administration a multi-dose effective amount of a peptide as set forth in SEQ ID NO: 1.

In an embodiment of the present disclosure, there is provided a method for delaying onset of Alzheimer's disease comprising intravenous administration of a multi-dose effective amount of a peptide as set forth in SEQ ID NO: 1, and concurrently at least one more neuroprotective agent.

In an embodiment of the present disclosure, there is provided a method for delaying onset of Alzheimer's disease comprising administering a single effective amount of a nanovesicle having size in the range of 50-600 nm comprising monomeric units of a peptide as set forth in SEQ ID NO: 1.

In an embodiment of the present disclosure, there is provided a method for delaying onset of Alzheimer's disease comprising administering a single effective amount of a nanovesicle having size in the range of 50-600 nm comprising monomeric units of a peptide as set forth in SEQ ID NO: 1, and concurrently at least one more neuroprotective agent.

In an embodiment of the present disclosure, there is provided a method for delaying onset of Alzheimer's disease comprising intravenous administration of a single effective amount of a nanovesicle having size in the range of 50-600 nm comprising monomeric units of a peptide as set forth in SEQ ID NO: 1.

In an embodiment of the present disclosure, there is provided a method for delaying onset of Alzheimer's disease comprising intravenous administration of a single effective amount of a nanovesicle having size in the range of 50-600 nm comprising monomeric units of a peptide as set forth in SEQ ID NO: 1, and concurrently at least one more neuroprotective agent.

In an embodiment of the present disclosure, there is provided a method for delaying onset of Alzheimer's disease comprising administering a multi-dose effective amount of a nanovesicle having size in the range of 50-600 nm comprising monomeric units of a peptide as set forth in SEQ ID NO: 1.

In an embodiment of the present disclosure, there is provided a method for delaying onset of Alzheimer's disease comprising administering a multi-dose effective amount of a nanovesicle having size in the range of 50-600 nm comprising monomeric units of a peptide as set forth in SEQ ID NO: 1, and concurrently at least one more neuroprotective agent.

In an embodiment of the present disclosure, there is provided a method for delaying onset of Alzheimer's disease comprising intravenous administration of a multi-dose effective amount of a nanovesicle having size in the range of 50-600 nm comprising monomeric units of a peptide as set forth in SEQ ID NO: 1.

In an embodiment of the present disclosure, there is provided a method for delaying onset of Alzheimer's disease comprising intravenous administration of a multi-dose effective amount of a nanovesicle having size in the range of 50-600 nm comprising monomeric units of a peptide as set forth in SEQ ID NO: 1, and concurrently at least one more neuroprotective agent.

In an embodiment of the present disclosure, there is provided a peptide as set forth in SEQ ID NO: 1 for prophylactic use in treating Alzheimer's disease.

In an embodiment of the present disclosure, there is provided a peptide as set forth in SEQ ID NO: 1 for curative use in treating Alzheimer's disease.

In an embodiment of the present disclosure, there is provided a nanovesicle having size in the range of 50-600 nm comprising monomeric units of a peptide as set forth in SEQ ID NO: 1 for prophylactic use in treating Alzheimer's disease.

In an embodiment of the present disclosure, there is provided a nanovesicle having size in the range of 50-600 nm comprising monomeric units of a peptide as set forth in SEQ ID NO: 1 for curative use in treating Alzheimer's disease.

In an embodiment of the present disclosure, there is provided a peptide as set forth in SEQ ID NO: 1 further modified for enhanced stability and/or imaging.

In an embodiment of the present disclosure, there is provided a peptide as set forth in SEQ ID NO: 1 which is biotinylated.

In an embodiment of the present disclosure, there is provided a peptide as set forth in SEQ ID NO: 1 which is attached to a fluorophore.

In an embodiment of the present disclosure, there is provided a nanovesicle having size in the range of 50-600 nm comprising monomeric units of a peptide as set forth in SEQ ID NO: 1 further modified for enhanced stability and/or imaging.

In an embodiment of the present disclosure, there is provided a nanovesicle having size in the range of 50-600 nm comprising monomeric units of a peptide as set forth in SEQ ID NO: 1, said peptide is biotinylated.

In an embodiment of the present disclosure, there is provided a nanovesicle having size in the range of 50-600 nm comprising monomeric units of a peptide as set forth in SEQ ID NO: 1, said peptide is attached to a fluorophore.

In an embodiment of the present disclosure, there is provided a peptide as set forth in SEQ ID NO: 1 which can self-assemble in-vitro to form nanovesicles having size in the range of 50-600 nm.

In an embodiment of the present disclosure, there is provided a peptide as set forth in SEQ ID NO: 1 which can self-assemble in-vivo to form nanovesicles having size in the range of 50-600 nm.

In an embodiment of the present disclosure, there is provided a method of preparing nanovesicle(s) having size in the range of 50-600 nm comprising monomeric units of a peptide as set forth in SEQ ID NO: 1.

Although the subject matter has been described in considerable detail with reference to certain preferred embodiments thereof, other embodiments are possible.

The present invention provides a novel hexapeptide Asn-Ala-Val-Ser-Ile-Gln (SEQ ID NO: 1) (NV, FIG. 1a) from activity dependent neuroprotective protein (ADNP) and synthesis this peptide as well as it's biotin and FITC-tagged peptide in laboratory through solid phase peptide synthesis method followed by purification through HPLC (FIG. 5-8) and characterization by Mass spectroscopy. The invention involves checking of the self-assembly behaviour of NV by molecular dynamic (MD) simulation. MD simulation of NV reveals atomic detail and the nature of self-assembly in solution. Initially, both two and four molecules of NV, denoted as orange (O) and green (G) were separated by 2 nm in the simulation box and simulated for 100 ns. It was found that the interactions between the NV's are dynamic in the initial stage of simulation (FIG. 1b). After simulation up to 20 ns, O and G peptides start interacting with each other in parallel orientation (FIGS. 1b and 9). After 40 ns of simulation, β-turn rich structure was observed through H-bonding interaction between Ser, Ile and Gln of O chain and Ala, Val and Ser of G chain respectively (FIGS. 1b and 9). Interestingly, at 50 ns, they form antiparallel β-sheet like structure through strong H-bonding interaction between Gln, Ile, Ser and Val of chain O and Ala, Val, Ser and Ile of chain G respectively (FIGS. 1b and 9). After 80 ns, stable β-sheet structure was formed due to H-bonding interaction between Val, Ser, Ile and Gln of chain O and Ile, Ser, Val and Ala of chain G respectively (FIGS. 1b and 9). Energy diagram confirms the stability of this β-sheet structure up to 100 ns (yellow colour region of FIG. 1c) simulation of NV. From the simulation it has been seen that five key amino acids Ala, Val, Ser, Ile and Gln in the hexapeptide backbone are responsible for the formation of this β-sheet structure (FIG. 1c). From the MD simulation, it was envisioned that the assembly process starts from the (3-turn like structure and rapidly converts to the β-sheet rich (FIGS. 1b and 9). In order to explore the self-assembly behavior of NV by various experimental techniques, firstly, the FT-IR spectroscopic studies of one hour incubated sample of NV was performed, which clearly shows β-sheet conformation as high absorption peak at 1628 cm-1 in Amide I region was observed, which is the signature peak for β-sheet conformation (FIG. 1e). Therefore, MD simulation result corroborate with the FT-IR result clearly indicates that NV spontaneously self-assembles in solution. These results further motivate to study the morphology of NV using transmission electron microscopy (TEM). Time dependent TEM images of 100 nM NV at 37° C. reveal extremely interesting process of self-assembly, which leads to the formation of nanovesicles (FIG. 1d). TEM image of day one reveals 10-40 nm width fibril, while in day two, fibrillary structures further self-assemble and form coiled nest like structure and finally in day three, further self-assembly results the formation of nano-vesicles (FIG. 10). In Alzheimer's disease (AD), microtubules are disrupted, which affects cytoskeleton organization, thus, protecting microtubule from disruption by small molecules is extremely important. Therefore, the present invention involves in investigation of whether NV can provide the stability in microtubule lattice through binding with microtubule. Docking results clearly indicate that NV binds with β-tubulin near to the taxol binding site through hydrophobic interaction and H-bonding interaction, which is important for microtubule stability (FIGS. 2a and 11). The binding partners (amino acids) between NV and tubulin were also found as follows; Asn (amide and amine group) of NV is H-bonded with two amino acids of Tubulin, one of them is Ser236 (—OH group) and the other one is Asp26 (—COOH group). On the other hand, Gln (amide group) of NV is H-bonded to Thr276 (—OH group) and —C═O group of both Ser277 and Arg278 of β-tubulin (FIGS. 2b and 12). In addition, NV adopts a bent like structure on the tubulin surface (FIGS. 2b and 12). The binding of NV near the taxol binding site was further confirmed by tubulin turbidity assay[2] and microtubule polymerization assay.[3] It was found that NV promotes the tubulin polymerization as the rate of increase of tubulin turbidity in presence of NV is higher than the control (FIG. 13) and also the rate of increment of DAPI fluorescence is also higher in presence of NV compare to control (FIG. 13). Above two results also supports the binding of NV to the taxol binding site of tubulin. Above results further motivates to study this binding through previously developed in vitro assay based on chemically modified micropatterned surface chemistry. In brief, in-house recently developed biotin micropatterned surface was immobilized with freshly prepared biotinylated-NV (Biotin-NV) onto the micropattern through neutravidin followed by incubation with tubulin mix (80:20 unlabeled tubulin and Alexa568 labeled tubulin) in the presence of GTP at 37° C. and observed using a TIRF microscope. After 30 min incubation on 37° C., localized binding of tubulin with Biotin-NV on immobilized biotin micropatterns was observed in red colored micropattern in 561 nm channel (FIG. 2c). Again, the present invention involves checking the binding of NV with polymerized tubulin. Here, FITC-labeled NV (FITC-NV) was used during polymerization of alexa-568 labeled tubulin in vitro in presence of GTP following previously described tubulin polymerization method and visualized polymerized microtubules using TIRF microscope. Microscopic images reveal green colored microtubules bundle at 488 nm laser (FIG. 2e), red colored microtubules at 561 nm laser (FIG. 2d) and yellow colored microtubule in merged channel (FIG. 20. This data clearly indicates that NV not only interacts with tubulin but also interacts with microtubule and doesn't perturb microtubule polymerization.

The present invention also involves exploring the properties that NV interacts with tubulin and microtubule from in vitro study, which further motivates to investigate whether NV interacts with intracellular tubulin/microtubule or not. For that purpose the microtubule co-localization study using confocal microscope was done. Experiment involves the incubation of FITC-NV with 3000-5000 densities of rat neuronal PC12 cells for 16 hours. Cells were washed and fixed with 4% paraformaldehyde and permeabilized with 0.2% triton-X. Then cellular microtubule was visualized as red colour using primary polyclonal anti-alpha tubulin antibody and fluorescent tagged secondary antibody. Nucleus was stained with Hoechst 33258. Interestingly, from confocal images yellow colored co-localized images inside the PC12 cells (FIG. 3d) was found, which clearly indicates the co-localization of FITC-labeled green colored peptide (FIG. 3b) and red colored microtubule networks in PC12 cells (FIG. 3a). FIG. 3c represents the nucleus of PC12 cells, stained by Hoechst. Therefore, above result clearly indicates that NV binds with intracellular tubulin/microtubule.

Again the present invention involves in checking whether this peptide has inhibitory effect against Aβ fibrillations. Initially, TEM study was used to understand the inhibition of Aβ fibrillations. For that purpose co-incubation of Aβ42 peptide and NV was done for 7 days. After 7 days incubation TEM image reveals nanovesicular structures with sporadic very short disrupted fiber like structure (FIG. 4b), while Aβ peptide alone in similar condition forms fibrils (FIG. 4a). This data clearly indicates that NV inhibits amyloid fibrillations in vitro. Since NV inhibits the fibril formation of Aβ peptide, how NV interacts with Aβ peptide was ascertained using molecular docking. Docking study clearly reveals that NV interacts with Aβ (PDB ID: 1IYT)[4] strongly through hydrophobic interaction and H-bonding interaction. It has been also found that the H-bonding helps in the interaction between the side chain of Asn (—NH2) of NV binds with —C=O group of Glu11. Further, —C=O group of Ala, Val, Ile, Gln interacts with —NH2 group of Gln15, —OH group of Val12, —NH2 group of Lys16, —OH group of Asp23 respectively (FIG. 4c and S10). It was described before that Aβ fibril formation occurs through antiparallel interaction of one Aβ monomer with the adjacent Aβ peptide through hydrophobic stretch of residues 17-21 of Aβ molecule.[5] Further, it was shown that Aβ peptide inhibitors binds to the hydrophobic stretch of residue 17-21[6-8], thus Aβ fibril formation can be prevented by inhibiting incoming Aβ molecule through blocking this site[9-11]. In present invention docking experiment have also found that NV binds to the hydrophobic region of residue 11-23 of Aβ. Therefore, Aβ peptide fibril formation is inhibited due to blocking the site by NV.

The present invention also involves investigation of whether NV exhibits neuroprotection against anti-NGF toxicity. It has been shown before that withdrawal of NGF from differentiated PC12 cells leads to overproduction of Aβ peptide.[12] Neuronal cell death and Aβ production in differentiated PC12 cells in response to NGF deprivation was completely blocked by inhibition of Aβ processing by β- and γ-secretase inhibitors or antibodies directed against Aβ peptide.[12] Moreover, experimental studies in NGF deficient transgenic mice and mechanistic studies on the antiamyloidogenic action of NGF signaling in primary cultures of neuronal cells revealed a fundamental link between NGF signaling deficiency and Alzheimer's neurodegeneration.[13] Thus, the neuroprotective potential of the inhibitor NV in neuronal cell line PC12 was studied.[14] These cells were differentiated in NGF containing medium for 5 days. On the fifth day they were treated overnight with anti-NGF along with different doses of inhibitor NV (FIG. 4d). NGF deprivation results in death of PC12 cells, and it has been widely used to study the mechanism of death of neurons.[15,16] Hence, this model is employed for assessing the neuroprotective potential of the inhibitor. The cells were observed under the microscope on the day following treatment; survival was assessed by intact nuclear counting assay (FIG. 4d). The results suggested that the inhibitor NV provided protection to the cells compared with cells subjected to NGF withdrawal. However, at higher concentrations, it did not provide better protection and showed toxicity to control cells. NV (5 μM) showed significant protection to cells compared with 10 and 20 μM (FIG. 4e). Importantly, cells maintained in the presence of 5 μM NV also retained overall neuronal morphology including neuronal processes even after NGF deprivation. Further, it was observed that inhibitor NV provided better protection to neuronal PC12 cells than NQ (positive control), to death induced by NGF deprivation.

DESCRIPTION OF FIGURES

FIG. 1: (a) Amino acid sequence of NV. (b) Snapshots from a MD simulation movie of NV demonstrating how it assembles rapidly to antiparallel β-sheet structure. (c) Secondary structure with the change of time reveals that Ala, Val, Ser, Ile and Gln of NV are involved in antiparallel β-sheet structure formation. (d) NV self-assembles to form nano-vesicles (Scale bar corresponds to 100 nm). (e) FT-IR spectrum of one hour incubated sample of NV reveals β-sheet structure.

FIG. 2: (a) Docking image reveals the interaction of NV with β-tubulin through hydrophobic interaction. (b) Specific interaction between the amino acids of β-tubulin and NV. (c) Microscopic image reveals that the tubulin specifically binds with NV, immobilized on biotin micropatterned surfaces. (d) Red colored microtubules represent alexa-568 labeled polymerized microtubules. (e) Green colored microtubules represent that FITC-NV binds with polymerized microtubules. (f) Merged image confirms the binding of FITC-NV with polymerized microtubules. Scale bar corresponds to 10 μm.

FIG. 3: (a) Red coloured microtubule networks of PC12 cells at 561 nm channel (b) Green tiny particles are distributed along the microtubule networks and all over the PC12 cells at 488 nm channel. (c) Blue coloured nucleus of PC12 cells at 405 nm channel. (d) Yellow coloured merged image reveals that NV binds along the intracellular microtubules of PC12 Cells. Scale bar corresponds to 30 μm.

FIG. 10: TEM image reveals the transformation of NV fibril to nanovesicular structure within 2 days incubation at 37° C. in PBS buffer containing 1% ammonium hydroxide. (a) 1 day. (b) 2 day and (c) 3 day incubated sample of 100 nMNV.

FIG. 14: (a) Image shows Aβ peptide alone forms antiparallel â-sheet structure. (b) NV peptide interacts with Aβ peptide and its interacting partners. (c) Zoomed image of NV interaction with Aβ peptide. (All the images are produced using pymol software:ThePyMOL Molecular Graphics System, Version 1.6.1 Schrödinger, LLC).

ADVANTAGES

Figure 4A:
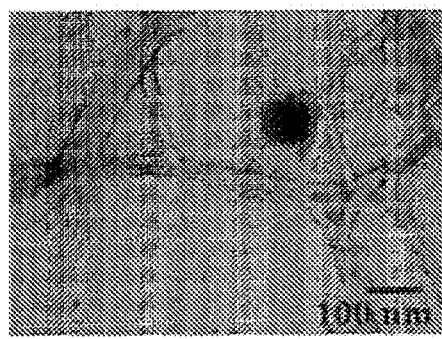
FIG. 4: (a) 100 nM Aβ peptide forms fiber after 7 days incubation at 37° C. in PBS buffer containing 1% ammonium hydroxide. (b) 7 days co-incubated sample of 100 nM Aβ peptide and 100 nMNV in PBS buffer at 37° C. shows nano-vesicles with very short fibril like structure. (c) NV interacts with Aβ peptide and its interacting partners. (d) Inhibitor NV protects neuronally differentiated PC12 cells against NGF deprivation. Neuronally differentiated PC12 cells were treated with anti-NGF in presence and absence of different doses of inhibitor NV for 20 h. Representative images show increased survival with retention of neuronal processes in PC12 cells treated with anti-NGF in presence of 5 μM NV. (e) Graphical representation of percentage of cell survival after anti-NGF treatment in presence of 5, 10 and 20 μM NV. (f) Inhibitor NV provides higher protection than inhibitor NQ. Graphical representation of percentage of cell viability following anti-NGF treatment in presence of 5 μM NV and 5 μM NQ. Data represented as mean±SEM of three independent experiments performed in triplicates. The asterisk denotes statistically significant differences between indicated classes: *p<0.05. Scale bar corresponds to 30 μm.
Figure 4B:
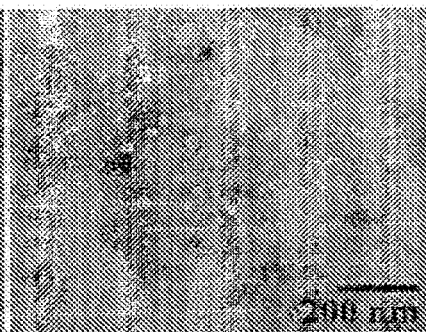
Figure 4C:
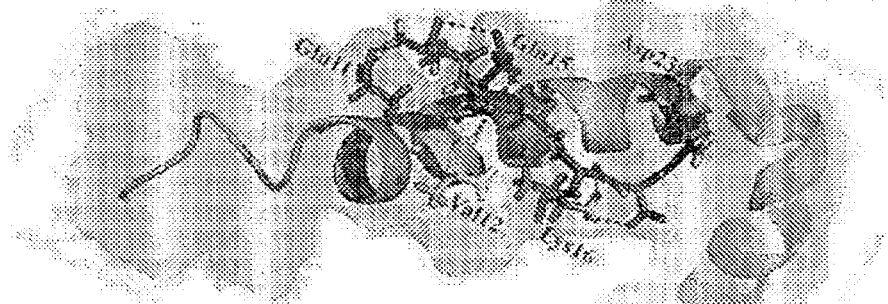
Figure 4D:
Figure 4E:
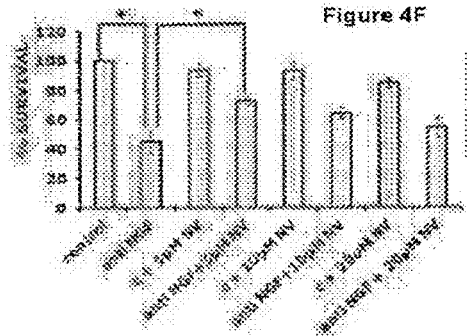
Figure 4F:
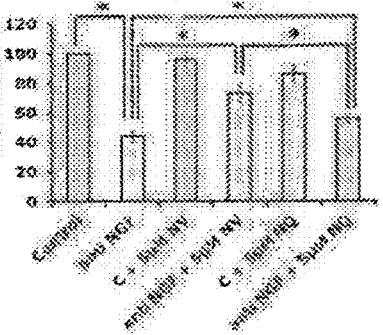
Figure 5:
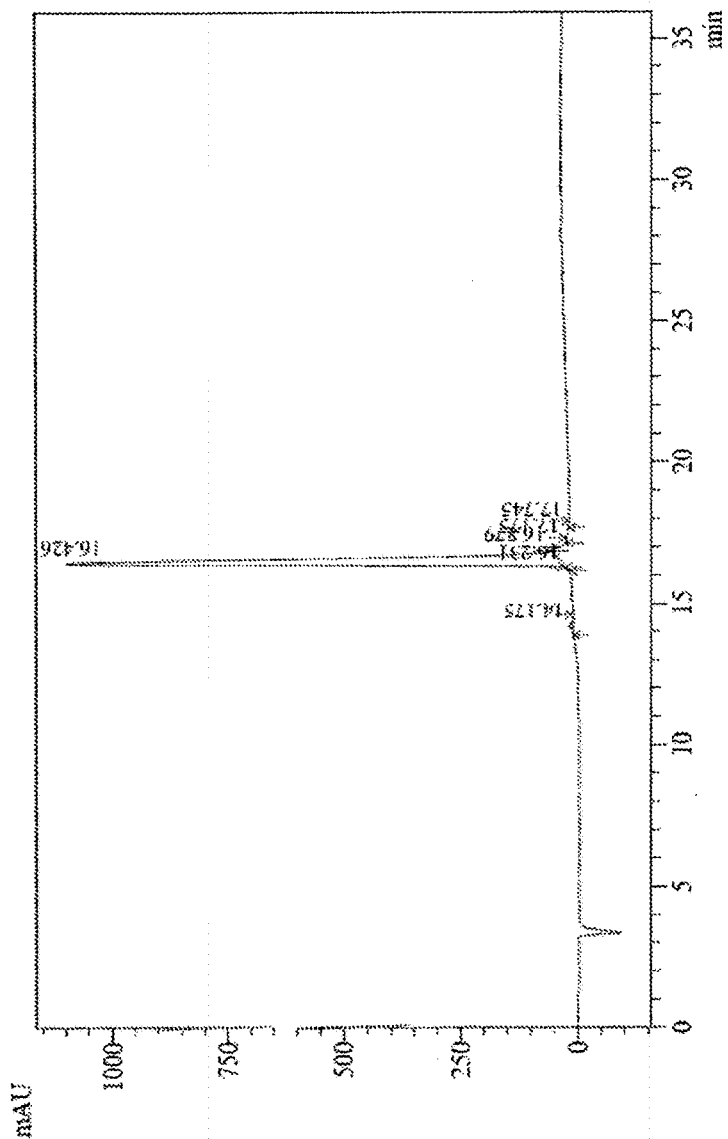
FIG. 5: HPLC chromatogram of NV shows purity >98%.
Figure 6:
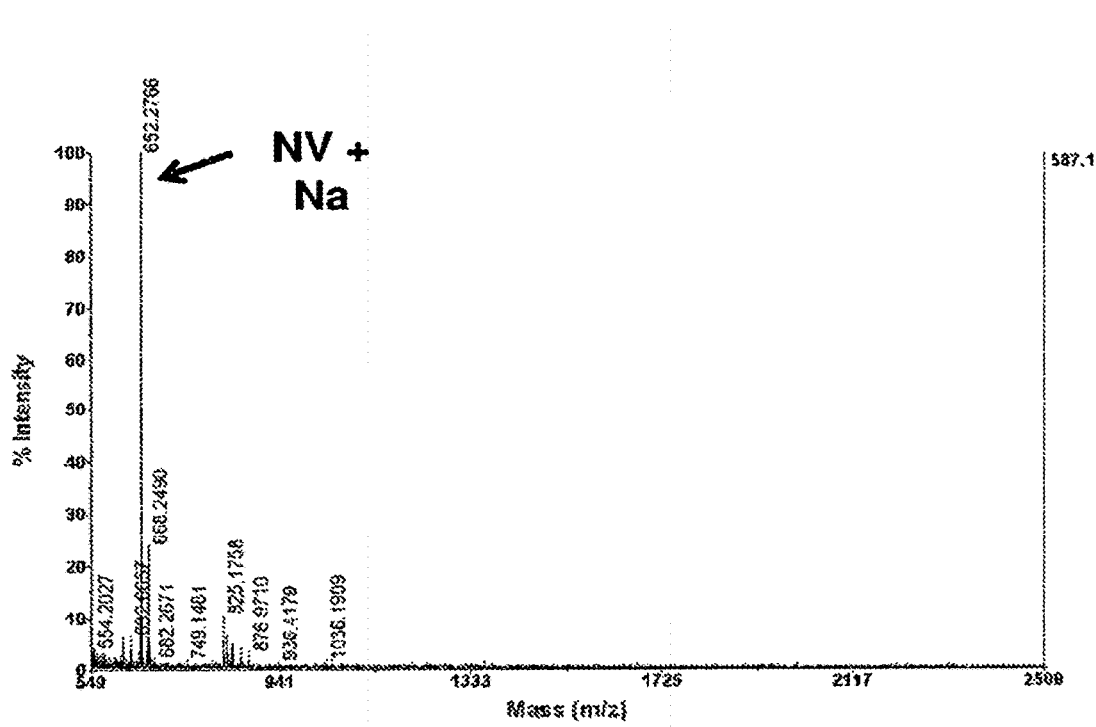
FIG. 6: MASS data of NV shows 630 Da.
Figure 7:
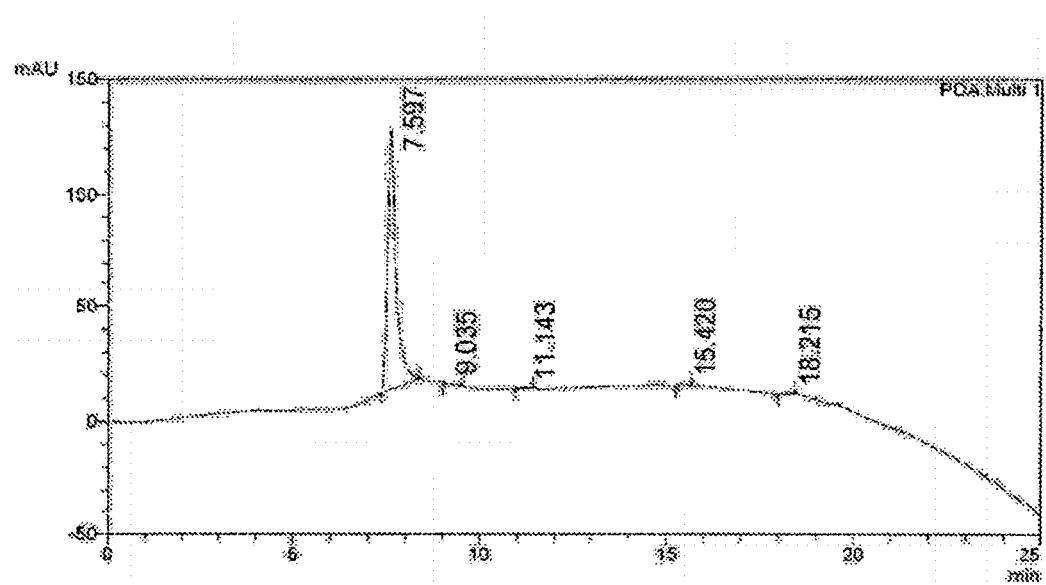
FIG. 7: HPLC chromatogram of Biotin-NV shows purity >97%.
Figure 8:
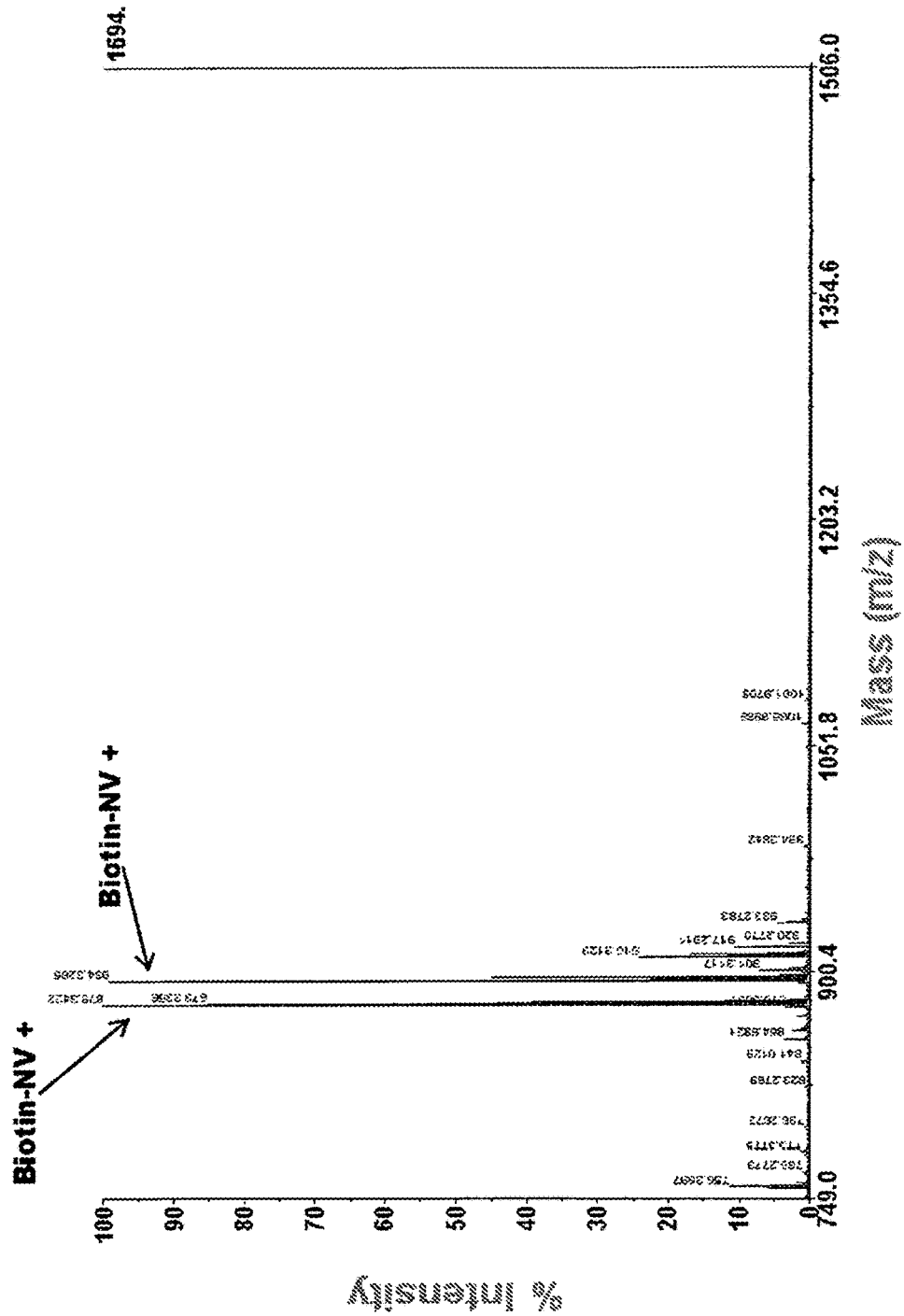
FIG. 8: MASS data of Biotin-NV shows 878 (855+Na$^+$) Da.
Figure 9:
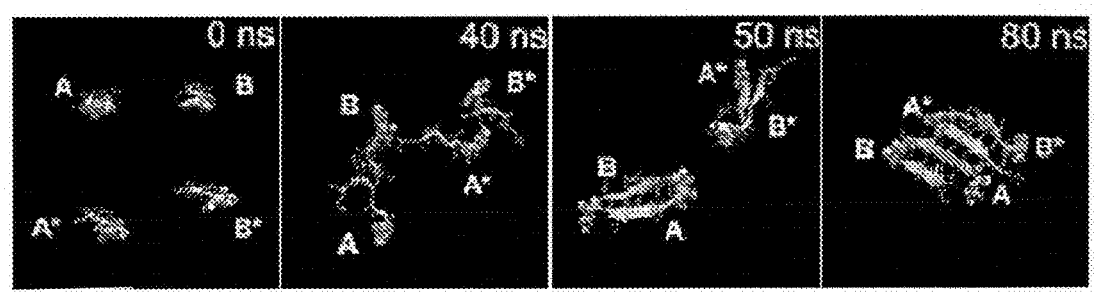
FIG. 9: Time lapse images from MD simulation of NVreveal that four hexapeptides rapidly transform to antiparallel β-sheet structure.
Figure 11A:
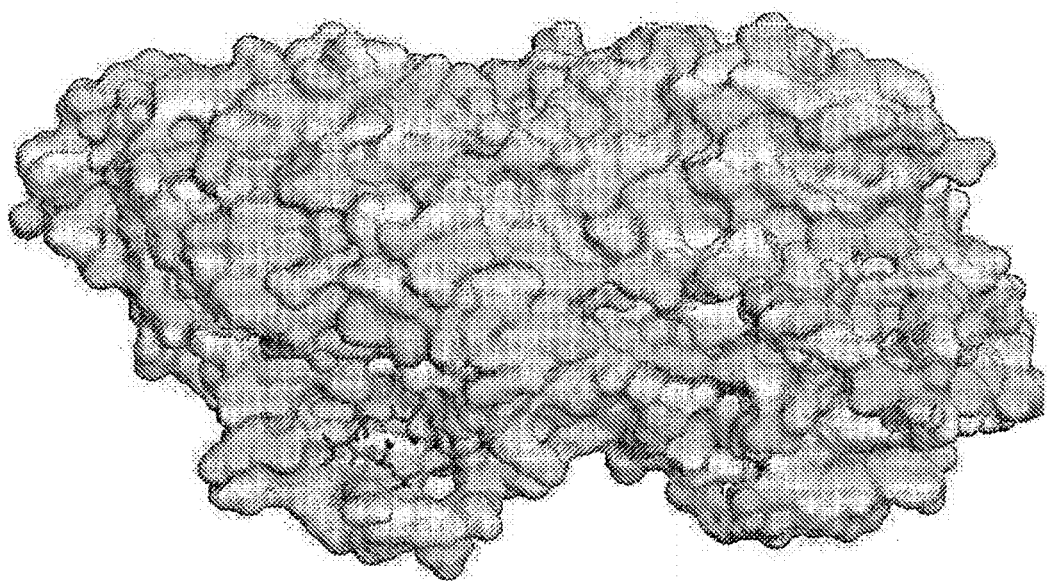
FIG. 11: (a) Docking result indicates that the hexapeptide binds with β-tubulin. (b) Docking result showing the amino acids of both NV and β-tubulin, involved in H-bonding.
Figure 11B:
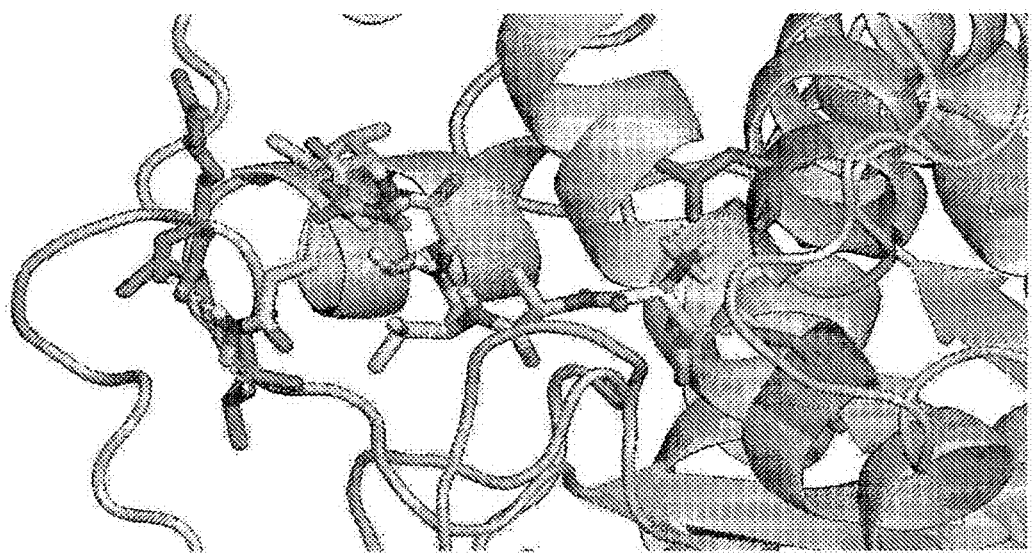
Figure 12A:
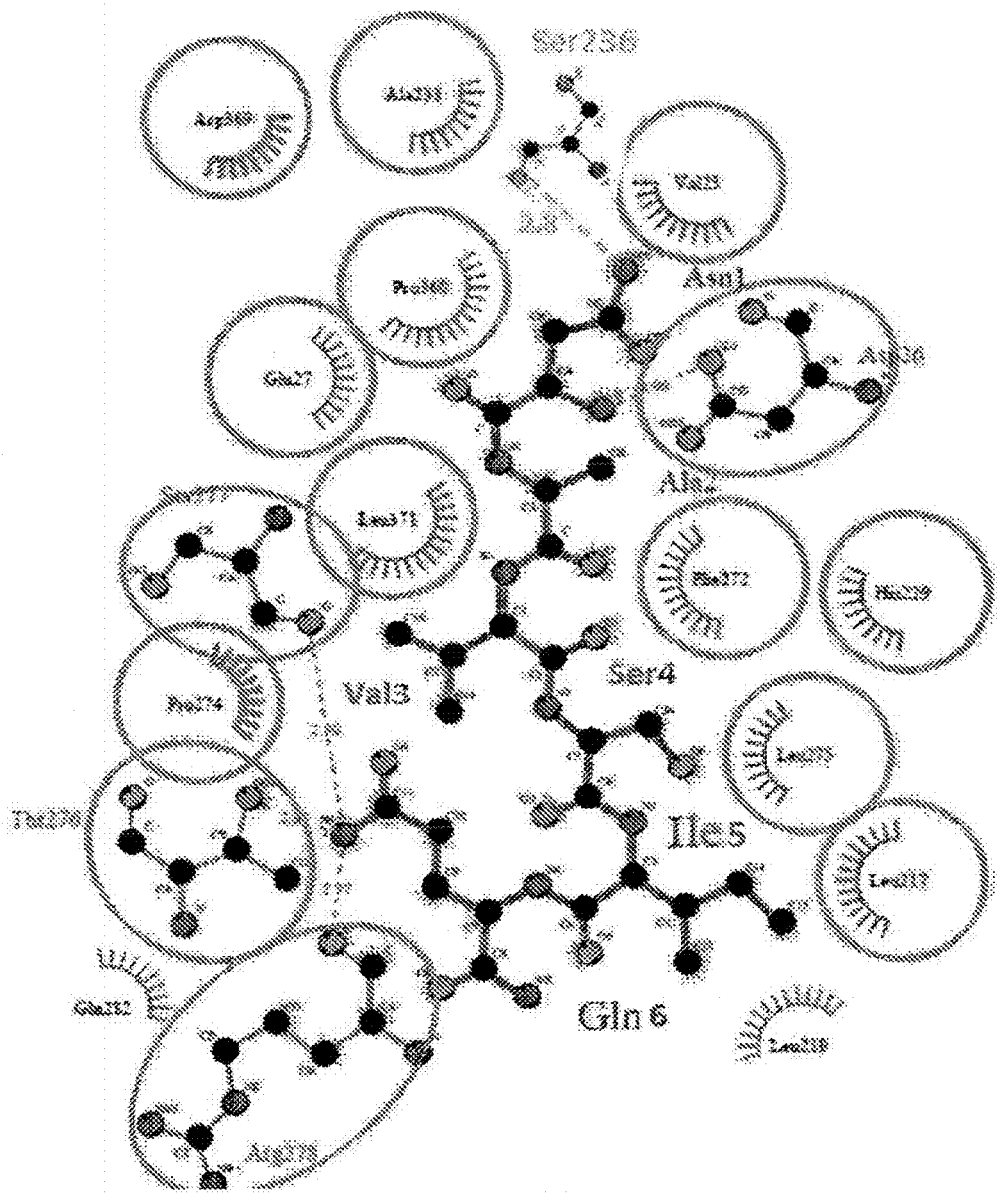
FIG. 12: (a) 2D view of binding site structure of taxol with tubulin dimer. (b) 2D view of hexapeptide binding site with tubulin dimer with the help of LIGPLOT.
Figure 12B:
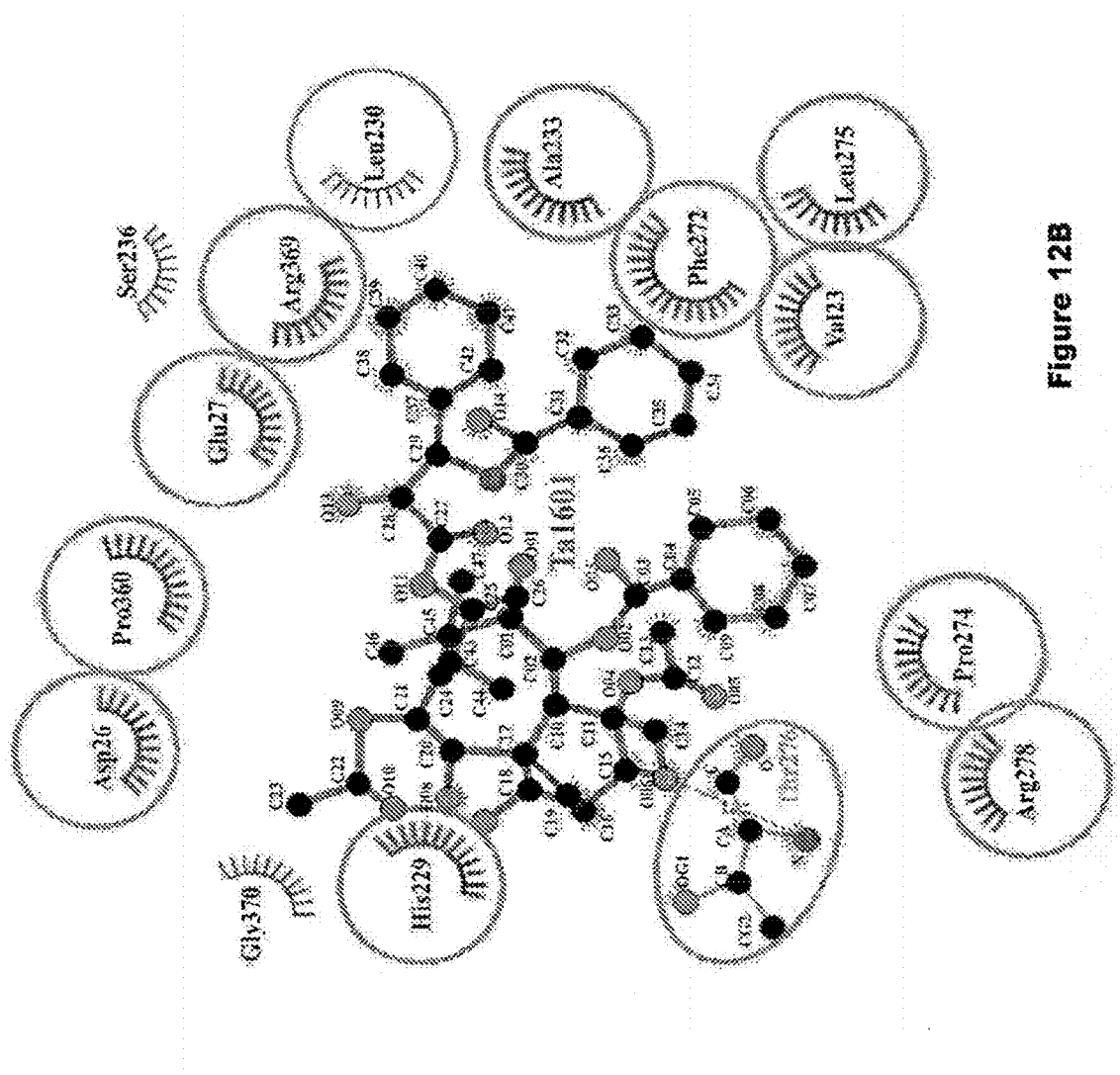
Figure 13A:
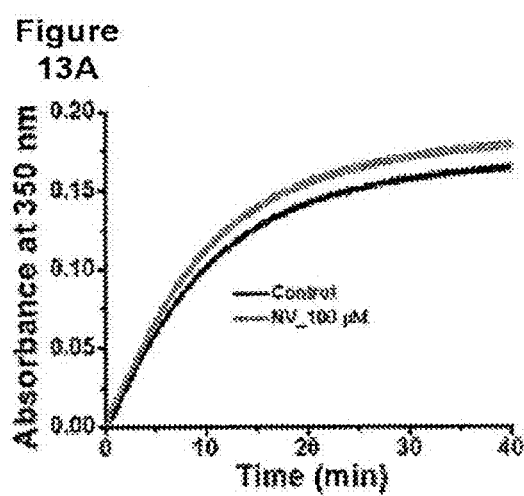
FIG. 13: (a) Tubulin turbidity assay in presence of 100 μM NV indicates that its helps in tubulin polymerization as tubulin turbidity increases in presence of 100 μM NV compares to control. (b) Microtubule assembly assay in presence of 100 μM NV also indicates that the rate of enhancement of DAPI fluorescence in presence of 100 μM NV is higher compare to control. These results indicate that NV promotes tubulin polymerization.
Figure 13B:
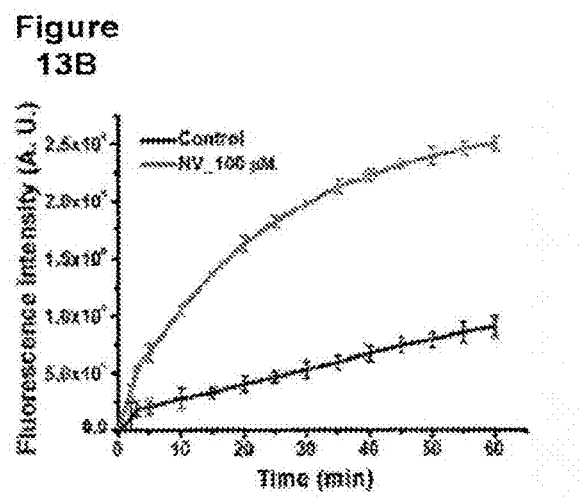

The present invention provides a new hexapeptide which act as a neuroprotector and having better neuroprotection than any other earlier reported peptide in this field.

Peptide based therapy always advantageous due to its excellent bioavailability.

It is simple to synthesize and the product is inexpensive.

The hexapeptide exhibits dual properties like binding with microtubule lattice and stabilize microtubule as well as provides excellent protection to neuron cells against Aβ.

It can be used as a potential therapy for Alzheimer's disease.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein. It is to be understood that this disclosure is not limited to particular methods, and experimental conditions described, as such methods and conditions may vary.

Example 1

Synthesis of Hexapeptide of SEQ ID NO: 1

"NV" (NH$_2$-NAVSIQ-NH$_2$; SEQ ID NO: 1), biotin-hexapeptide "Bio-NV" (Biotin-NAPVSIPQ-NH$_2$; SEQ ID NO: 2), "FITC-NV" (FITC-NAVSIQ-NH$_2$; SEQ ID NO: 1) and octapeptide "NQ" (NH$_2$-NAPVSIPQ-NH$_2$) (SEQ ID NO: 2) have been performed by solid phase peptide synthesis method using Rink Amide AM resin in peptide synthesizer. Crude peptides were purified by HPLC and characterized by MALDI Mass Spectroscopy.

Example 2

Transmission Electron Microscopy (TEM)

A 10 μL aliquot of the 100 nM solution of both 'NV' and Aβ peptide was incubated individually as well as together at 37° C. After 0, 1, 2 and 7 days, the incubated solutions were placed on a 300 mesh copper grid from ProSciTech. After 1 minute, excess solution was removed and the grid was washed with water followed by staining with 2% Uranyl acetate in water. Samples were viewed using a TECNAI G2 SPIRIT BIOTWIN CZECH REPUBLIC 120 KV electron microscope operating at 80 kV.

Example 3

Fourier Transform Infrared Spectroscopy

The freshly prepared peptide was incubated for one hour, lyophilized and FT-IR spectroscopic analysis was carried out in a Perkin-Elmer Spectrum 100 FT-IR spectrometer using KBr pellets. Spectra of these pellets were recorded and accumulated of 5 times scan with speed 0.2 cm/s at a resolution of 1.6 cm$^{-1}$ in a Perkin-Elmer Spectrum 100 series Spectrometer. The LiTaO3 detector was used for data plotting. Each time background correction was performed to eliminate interference from air (or any other parameters).

Example 4

Tubulin Polymerization Assay/Tubulin Turbidity Assay

Tubulin turbidity assay was performed in the presence of GTP. 20 μM tubulin, 4 mM GTP, 10% dimethyl sulfoxide and 100 μM NV were mixed in Brinkley Reassembly Buffer 80 (BRB 80) in ice and injected into 37° C. heated quartz cuvettes of path length 10 mm. The turbidity was measured by measuring absorbance of the solution at 350 nm for 40 min in the UV-Vis Spectrophotometer (G6860A Cary 60 UV-Vis Spectrophotometer, Agilent Technologies). DMSO was used to initiate the polymerization. The control experiment was carried following the same procedure in the absence of NV.

Example 5

Microtubule Assembly Assay

It was carried out following previously described procedure. A mixture of 10 μM DAPI in BRB80 buffer containing 100 μM tubulin, 10 mM GTP and 100 μM NV was prepared. The solution was excited at 355 nm wavelength at 37° C. and the emission spectra of the solution was recorded in region from 400 nm to 600 nm wavelength for 60 min in five min time interval in Quanta Master Spectrofluorometer (QM-40), which is equipped with peltier for controlling the temperature during experiment. Control experiment was carried out under same condition in absence of NV. The data was calculated in origin Pro 8.5 software.

Example 6

Hexapeptide NV Binding with Microtubule at Tubulin Polymerization

Mixture 1: Alexa Fluor 568-labeled tubulin (0.5 μL, 15 mg mL$^{-1}$, 65% labelling ratio), Tubulin (2 μL, 20 mg mL$^{-1}$), FITC-NV (0.5 μL, 1 mM), GTP (0.2 μL, mM) and BRB80 (46.8 μL; 80 mM PIPES, 1 mM EGTA; 1 mM MgCl2, pH adjusted to 6.8 by using concentrated KOH solution) were mixed on ice. The mixture was incubated for 30 min on 37° C. water bath.

Mixture 2: Taxol (0.4 μL, 1 mM) and BRB80 (180 μL) were mixed.

Final Mixture: After 30 min incubation 50 µL warmed mixture 2 was added into mixture 1. Then this mixture was separated in a table top centrifuge (7 min, 12000 rpm, Eppendorf 5810R bench-top centrifuge, rotor type F-34-6-38). The coloured pellet was resuspended in warm mixture 2. 10 µL resuspended solution of microtubule was placed on glass cover slip and imaged under inverted fluorescence microscope (NIKON Ti-U) in 40× magnification using ANDOR iXON3 camera.

Example 7

Hexapeptide 'NV' and Aβ42 Interaction

1 µM solution of Aβ42 alone and equal volume of 1 µM solution of Aβ 42 and 100 nM solution of 'NV' were incubated differently for 7 days. After 7 days both solutions were deposited in carbon coated TEM grid and the morphology was studied under transmission electron microscope.

Example 8

Hexapeptide 'NV'-Tubulin Interaction Study on Biotin Micropatterned Surface

Biotin micropatterned surfaces were prepared as previously described method. A flow chamber of around 5 µL was built from one biotin-patterned glass surface and one poly-L-lysine (PLL)-PEG passivated counter glass, separated by two strips of double sticky tape (Tesa). Flow chamber was equilibrated with BRB80 and incubated with β-casein for 10 min followed by washing with 20 µL BRB80 for complete removal of unbound β-casein. 100 nM neutravidin was flowed into the flow chamber and incubated for 10 min followed by removal of excess neutravidin with 20 µL BRB80. 1 mM biotinylated-hexapeptide (Bio-NV) in BRB80 was flowed into the flow chamber and incubated for 10 min and washed unbound peptide by 20 µL BRB80. Then, the flow chamber was filled with 18.5 µM tubulin mix (80:20 unlabeled tubulin and Alexa568 tubulin) in BRB80 supplemented with 3 mM GTP, 10 mM MgCl2, and an oxygen scavenger system (50 mM glucose, 1 mg mL$^{-1}$ glucose oxidase, and 0.5 mg mL$^{-1}$ catalase) on an ice cold metal block and placed to the TIRF microscope at 37° C. Then flow chamber was imaged using an IX-81 total internal reflection fluorescence (TIRF) microscope (Olympus) with a 60×TIRFM objective (Olympus; Hamburg, Germany) and an Andor iXon3 897 Camera. Control experiment was performed, following previously described method without immobilizing 'Bio-NV' on biotin micropatterned surface.

Example 9

Hexapeptide 'NV' and Cellular Microtubule Interaction Study by Confocal Microscope PC12 neural cells having cell density 3000-5000/coverslip were grown on cover-slip and harvested overnight. Then media has been changed with the treatment solution containing 100 µM of FITC-NV peptide. After 16 h of incubation, complete media was aspired out and cover-slip was washed with serum free media. Cells were fixed with 4% par formaldehyde for 1 h and incubated with 0.2% triton-X and 5% BSA in PBS for 1 h. After a single wash with 1×PBS cells were incubated with polyclonal anti-α-tubulin IgG antibody (Abcam) with dilution 1:300 for 2 hours. Then cells were washed with PBS and incubated with secondary antibody (Cy3.5 pre-absorbed goat anti-rabbit IgG; Abcam) having dilution 1:600 for 2 hours. Cells were washed with 1×PBS followed by incubation with Hoechst 33258 from Calbiochem (1 µg/mL) for 30 minutes before imaging. Microscopy image was taken with confocal microscope with a 60× objective (Olympus) and an Andor iXon3 897 EMCCD camera in bright field, 405, 488 and 561 nm wavelength laser lights.

Example 10

Cell Culture

Rat pheochromocytoma cells (PC12) cells were cultured as described previously (ESI) in RPMI medium supplemented with 10% heat-inactivated horse serum (HS) and 5% heat-inactivated fetal bovine serum. Neuronal differentiation of these cells was induced by NGF (100 ng/mL) in medium containing 1% horse serum for 6 days before the treatment, as previously described.

Example 11

Cell Viability Assay

The cell viability was checked by the intact nuclear counting method. This assay was performed as described previously. In brief, a detergent containing the buffer that dissolved only the plasma membrane was added to the cells, the nuclear membrane thus remained intact. The intact nuclei were then counted on a haemocytometer under a light microscope. The number of live cells was expressed as percentage of the total cell population.

Example 12

MD Simulation

For simulation study single peptide was kept at the centre of cubic box solvated by 2946 Simple Point Charge (SPC) water model. One Chlorine atom in 4.5 nm cubic box was used to neutralize the system. Two random coil peptides, separated by 2.0 nm were solvated by 2944 Simple Point Charge (SPC) water model. Two Chlorine atoms were used to neutralize the system in 4.5 nm cubic box. For simulation study GROMACS version 4.5.5 was used. Gromos 96 53a6 force field was applied for peptides. Periodic boundary conditions were applied in all three directions. 0.9 nm cut-off radii were set for electrostatic interactions and 1.4 nm for Lennard-Jones interactions. Long-range electrostatics interactions were tested using Particle-Mesh Ewald (PME) method. Simulation was performed at a time step of 2 fs. The first phase involved the simulating for 500 ps under a constant volume (NVT) ensemble. Using V-rescale coupling method Protein and non-protein atoms were coupled to separate coupling baths and temperature maintained to 310 K. Following NVT equilibration, 1 ns of constant-pressure (NPT) equilibration was performed using Parrinello-Rahman coupling method. Relaxation time of 1 ps and 0.1 ps were used for NPT and NVT respectively. Then production run was performed for 100 ns. LINCS algorithm was used to constrain bond lengths. For four molecules we used similar method as described before and details described in ESI.

Example 13

Docking

Autodock-Vina software version 1.1.2 was used for blind docking. A 98×60×64 affinity grid box was centred on the receptor (1JFF) for tubulin-NV peptide docking and a 40×26×54 affinity grids were centred on the receptor Alzheimer amyloid beta peptide (PDB ID: 1IYT) for Aβ-NV peptide docking interaction. The Protein-Peptide interaction was represented using 2D interaction plot, was plotted with the help of Ligplot (ESI).

Example 14

Data Analysis

Microscopic images were analysed using Image J software.

REFERENCES

1. Biswas, A., Kurkute, P., Jana, B., Laskar, A., Ghosh, S. (2014) An amyloid inhibitor octapeptide forms amyloid type fibrous aggregates and affects microtubule motility. Chem Commun. 50, 2604-2607.
2. Chakraborti, S., Das, L., Kapoor, A. N., Dwivedi, V., Poddar, A., Chakraborti, G., Janik, M., Basu, G., Panda, D., Chakrabarti, P., Surolia, A., and Bhattacharyya, B. (2011) Curcumin recognizes a unique binding site of tubulin. J. Med. Chem. 54, 6183-6196.
3. Bonne, D., Heusele, C., Simon, C., and Pantaloni, D. (1984) 4',6-Diamidino-2-phenylindole, a fluorescent probe for tubulin and microtubules. J. Biol. Chem. 260, 2819-2825.
4. Crescenzi, O., Tomaselli, S., Guerrini, R., Salvadori, S., D'Ursi, A. M., Temussi, P. A., and Picone, D. (2002) Solution structure of the alzheimer amyloid b-peptide (1-42) in an apolar microenvironment. Eur. J. Biochem. 269, 5642-5648.
5. Gordon, D. J., Sciarretta, K. L., and Meredith, S. C. (2001) Inhibition of beta-Amyloid (40) Fibrillogenesis and disassembly of beta-amyloid (40) fibrils by short beta-amyloid congeners containing N-methyl amino acids at alternate residues. Biochemistry 40, 8237-8245.
6. Bieler, S., and Soto, C. (2004) â-Sheet Breakers for Alzheimer's Disease Therapy. Curr. Drug Targets 5, 553-558.
7. Lülus, T., Ritter, C., Adrian, M., Riek-Loher, D., Bohrmann, B., Döteli, H., Schubert, D., and Riek, R. (2005) 3D structure of alzheimer's amyloid-beta (1-42) fibrils. Proc. Natl. Acad. Sci. USA 102, 17342-17347.
8. Sanphui, P., Pramanik, S. K., Chatterjee, N., Moorthi, P., Banerji, B., and Biswas. S. C. (2013) Efficacy of cyclin dependent kinase 4 inhibitors as potent neuroprotective agents against insults relevant to Alzheimer's disease. PLoS ONE 8, e78842. doi:10.1371/journal.pone.0078842
9. Barrow, C. J., and Zagorski, M. G. (1991) Solution structures of beta peptide and its constituent fragments: relation to amyloid deposition. Science 253, 179-182.
10. Masters, C. L., Simms, G., Weinman, N. A., Multhaup, G., McDonald, B. L., and Beyreuther, K. (1985) Amyloid plaque core protein in Alzheimer disease and Down syndrome. Proc. Natl. Acad. Sci. USA 82, 4245-4249.\
11. LaFerla, F. M., Green, K. N., and Oddo, S. (2007) Intracellular amyloid-beta in Alzheimer's disease. Nature Rev. Neurosci. 8, 499-509.
12. Matrone, C., Di Luzio, A., Meli, G., D'Aguanno, S., Severini, C., Ciotti, M. T., Cattaneo, A., and Calissano, P. (2008) Activation of the amyloidogenic route by NGF deprivation induces apoptotic death in PC12 cells. J. Alzheimer's Dis. 13, 81-96.
13. Cattaneo, A., and Calissano, P. (2012) Nerve growth factor and Alzheimer's disease: new facts for an old hypothesis. Mol. Neurobiol. 46, 588-604.
14. Greene, L. A., and Tischler, A. S. (1976) Establishment of a noradrenergic clonal line of rat adrenal pheochromocytoma cells which respond to nerve growth factor. Proc. Natl. Acad. Sci. U.S.A 73, 2424-2428.
15. Biswas, S. C., and Greene, L. A. (2002) Nerve growth factor (NGF) down-regulates the Bcl-2 homology 3 (BH3) domain-only protein Bim and suppresses its proapoptotic activity by phosphorylation. J. Biol. Chem. 277, 49511-49516.
16. Xu, Z., Maroney, A. C., Dobrzanski, P., Kukekov, N. V., and Greene, L. A. (2001) The MLK family mediates c-Jun N-terminal kinase activation in neuronal apoptosis. Mol. Cell. Biol. 21, 4713-4724.

We claim:

1. A nanovesicle having a size in the range of 50-600 nm comprising monomeric units of a peptide consisting of the amino acid sequence as set forth in SEQ ID NO:1.

2. A peptide consisting of the amino acid sequence as set forth in SEQ ID NO: 1 further modified for imaging.

3. The nanovesicle as claimed in claim 1, further modified for imaging.

* * * * *

SEQUENCE LISTING

```
<160> NUMBER OF SEQ ID NOS: 2

<210> SEQ ID NO 1
<211> LENGTH: 6
<212> TYPE: PRT
<213> ORGANISM: artificial sequence
<220> FEATURE:
<223> OTHER INFORMATION: hexapeptide

<400> SEQUENCE: 1

Asn Ala Val Ser Ile Gln
1               5

<210> SEQ ID NO 2
<211> LENGTH: 8
<212> TYPE: PRT
<213> ORGANISM: artificial sequence
<220> FEATURE:
<223> OTHER INFORMATION: octapeptide

<400> SEQUENCE: 2

Asn Ala Pro Val Ser Ile Pro Gln
1               5
```